United States Patent
Boukhny et al.

(10) Patent No.: US 6,179,808 B1
(45) Date of Patent: Jan. 30, 2001

(54) METHOD OF CONTROLLING THE OPERATING PARAMETERS OF A SURGICAL SYSTEM

(75) Inventors: Mikhail Boukhny, Laguna Beach; Michael D. Morgan, Costa Mesa, both of CA (US)

(73) Assignee: Alcon Laboratories, Inc., Fort Worth, TX (US)

(*) Notice: Under 35 U.S.C. 154(b), the term of this patent shall be extended for 0 days.

(21) Appl. No.: 09/336,230

(22) Filed: Jun. 18, 1999

(51) Int. Cl.$^7$ .................................................. A61M 31/00
(52) U.S. Cl. ............................................................ 604/65
(58) Field of Search ........................... 604/19, 27, 30–31, 604/35, 65–67

(56) References Cited

U.S. PATENT DOCUMENTS

| | | |
|---|---|---|
| 3,589,363 | 6/1971 | Banko et al. . |
| 4,029,094 * | 6/1977 | Winicki . |
| 4,184,510 | 1/1980 | Brumbach . |
| 4,223,676 | 9/1980 | Wuchinich et al. . |
| 4,246,902 | 1/1981 | Martinez . |
| 4,493,694 | 1/1985 | Wuchinich . |
| 4,515,583 | 5/1985 | Sorich . |
| 4,589,415 | 5/1986 | Haaga . |
| 4,609,368 | 9/1986 | Dotson, Jr. . |
| 4,869,715 | 9/1989 | Sherburne . |
| 4,909,786 * | 3/1990 | Gijselhart et al. . |
| 4,922,902 | 5/1990 | Wuchinich et al. . |
| 4,989,583 | 2/1991 | Hood . |
| 5,154,694 | 10/1992 | Kelman . |
| 5,160,317 | 11/1992 | Costin . |
| 5,279,547 | 1/1994 | Costin . |
| 5,342,313 | 8/1994 | Campbell et al. . |
| 5,520,633 | 5/1996 | Costin . |
| 5,591,127 | 1/1997 | Barwick, Jr. et al. . |
| 5,700,240 | 12/1997 | Barwick, Jr. et al. . |
| 5,733,256 * | 3/1998 | Costin . |
| 5,766,146 | 6/1998 | Barwick, Jr. et al. . |
| 5,836,909 | 11/1998 | Cosmescu . |

FOREIGN PATENT DOCUMENTS

| | | |
|---|---|---|
| 2 727 847 | 6/1996 | (FR) . |
| WO/90 08562 | 8/1990 | (WO) . |
| WO 99/45868 | 9/1999 | (WO) . |

* cited by examiner

*Primary Examiner*—Sharon Kennedy
*Assistant Examiner*—Catherine Serke
(74) *Attorney, Agent, or Firm*—Jeffrey S. Schira

(57) ABSTRACT

A control system for a surgical system that includes an irrigation fluid flow sensing capability. The sensing capability may be placed in the control console or in the handpiece. Irrigation flow measurements provided by the sensing capability allows the control system to vary irrigation pressure and/or flow, aspiration pressure and/or flow and power supplied to the handpiece more accurately than prior art sensors that monitor aspiration flow.

4 Claims, 7 Drawing Sheets

METHOD OF CONTROLLING THE OPERATING PARAMETERS OF A SURGICAL SYSTEM

BACKGROUND OF THE INVENTION

This invention relates generally to the field of microsurgery and more particularly to a control system for an ophthalmic surgery system.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

The preferred surgical technique is to make the incision into the anterior chamber of the eye as small as possible in order to reduce the risk of induced astigmatism. These small incisions result in a very tight wounds that squeeze the irrigating sleeve tightly against the vibrating tip. Friction between the irrigating sleeve and the vibrating tip generates heat, but the risk of the tip overheating and causing a burn to the tissue is reduces by the cooling effect of the aspirated fluid flowing inside the tip. When the tip becomes occluded with tissue, this aspiration flow can be reduced or eliminated, allowing the tip to heat up.

Prior art devices have used sensors that detect large rises in aspiration vacuum, and predict occlusions based on vacuum rise. Based on this sensed occlusion, power to the handpiece may be reduced and/or irrigation and aspiration flows can be increased. See U.S. Pat. Nos. 5,591,127, 5,700,240 and 5,766,146 (Barwick, Jr., et al.), the entire contents of which being incorporated herein by reference. Increased vacuum levels in the aspiration line, however, do not necessarily indicate that the flow of cooling fluid around the tip has been cut off. Even with the tightest incisions, some irrigating fluid will leak out between the wound and the outside of the irrigating sleeve. The wound leakage also provides addition cooling flow to the incision site, and measuring rises in aspiration vacuum alone does not necessarily indicate that a potential for a corneal burn exists. Therefore, power to the handpiece may be interrupted prematurely.

Therefore, a need continues to exist for a control system for a surgical handpiece that utilizes a better indication of fluid flow at the tip for the control of ultrasonic power levels.

BRIEF SUMMARY OF THE INVENTION

The present invention improves upon the prior art by providing a control system for a surgical system that includes an irrigation fluid flow sensing capability. The sensing capability may be placed in the control console or in the handpiece. Irrigation flow measurements provided by the sensing capability allows the control system to vary irrigation pressure and/or flow, aspiration pressure and/or flow and power supplied to the handpiece more accurately than prior art sensors that monitor aspiration flow.

Accordingly, one objective of the present invention is to provide a surgical console control system.

Another objective of the present invention is to provide a surgical console control system having an irrigation flow sensing capability.

Another objective of the present invention is to provide a surgical console control system that provides more accurate control of the handpiece operating parameters.

Another objective of the present invention is to provide a surgical console control system that provides more accurate control of the infusion operating parameters.

Another objective of the present invention is to provide a surgical console control system that provides more accurate control of the aspiration operating parameters.

DETAILED DESCRIPTION OF THE INVENTION

Figure 1:
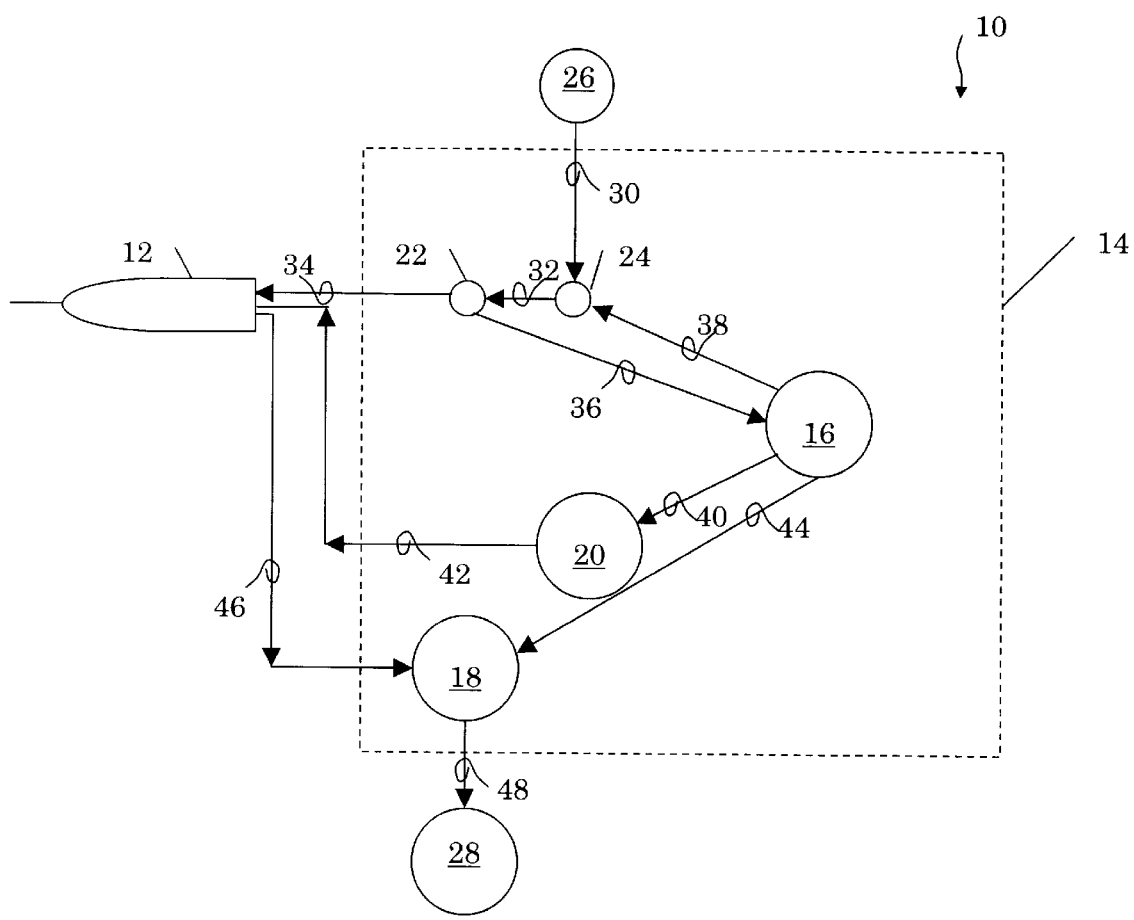
FIG. 1 is a block diagram of a first embodiment of a control system that can be used with the present invention showing the flow sensor in the instrument.

As seen in FIG. 1, in a first embodiment of the present invention, control system 10 for use in operating handpiece 12 includes control console 14. Control console 14 generally includes control module or CPU 16, aspiration pump 18, handpiece power supply 20, irrigation flow sensor 22 and valve 24. Console 14 may be any commercially available surgical control console such as the ACCURUS® surgical system available from Alcon Laboratories, Inc., Fort Worth, Tex. CPU 16 may be any suitable microprocessor, micro controller, computer or digital logic controller. Pump 18 may be any suitable pump, such as a peristaltic, diaphragm or venturi pump. Power supply 20 may be any suitable ultrasound driver, such as incorporated in the ACCURUS® surgical system available from Alcon Laboratories, Inc., Fort Worth, Tex. Sensor 22 may be any commercially available flow sensor, such as Models Nos. T101D or T201D available from Transonic Systems, Inc., Ithaca, N.Y. Valve 24 may be any suitable valve such as a solenoid-activated pinch valve. Infusion source 26 may be any commercially available irrigation solution provided in bottles or bags.

In use, sensor 22 is connected to handpiece 12 and infusion fluid source 26 through irrigation lines 30, 32 and 34. Sensor 22 measures the flow of irrigation fluid from source 26 to handpiece 12 and supplies this information to CPU 16 through cable 36. The irrigation fluid flow data may be used by CPU 16 to control the operating parameters of console 14 using software commands that are well known in the art. For example, CPU 16 may, through cable 40, vary the output of power supply 20 being sent to handpiece 12 though power cable 42. CPU 16 may also use data supplied by sensor 22 to vary the operation of pump 18 through cable 44, which aspirates fluid from handpiece 12 through line 46 and into collection container 28 through line 48. CPU 16 may also use data supplied by sensor 22 and the applied output of power supply 20 to provide audible tones to the user.

Figure 2:
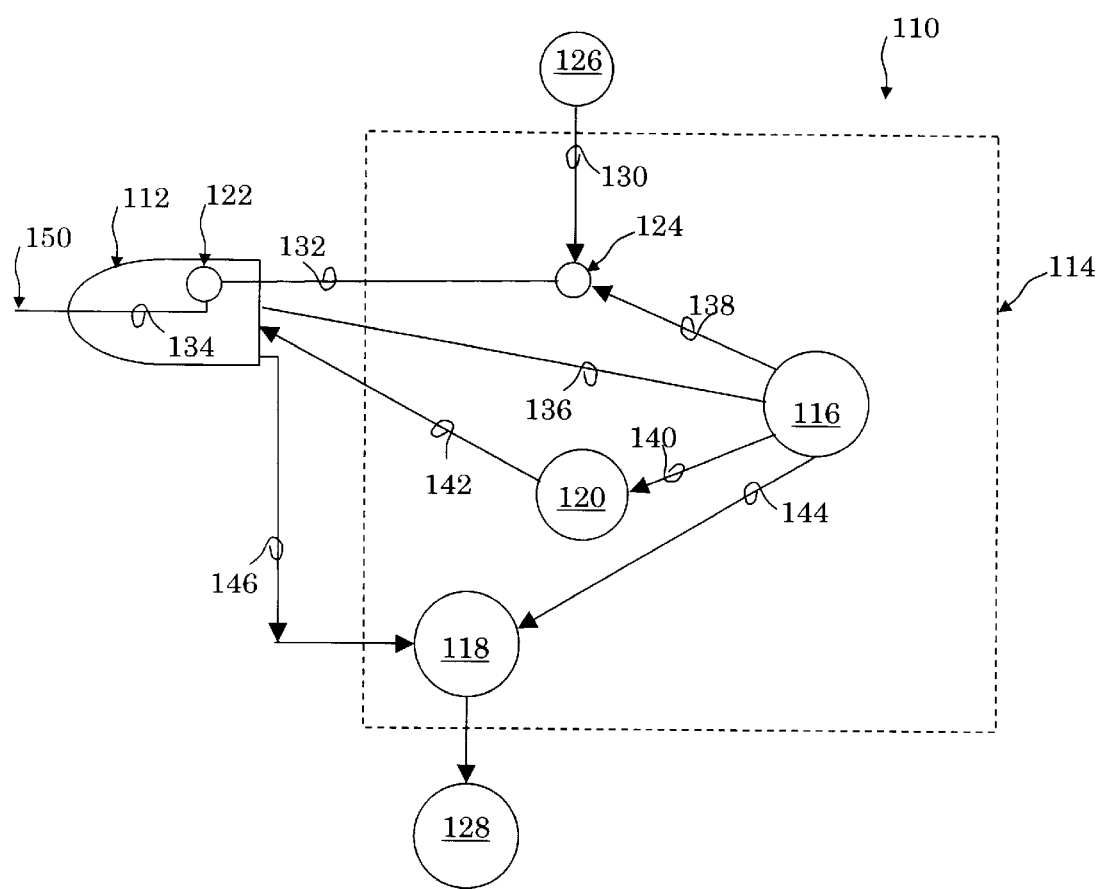
FIG. 2 is a block diagram of a second embodiment of a control system that can be used with the present invention showing the flow sensor in the handpiece.

As seen in FIG. 2, in a second embodiment of the present invention, control system 110 for use in operating handpiece 112 includes control console 114. Control console 114 generally includes control module or CPU 116, aspiration pump 118, handpiece power supply 120 and valve 124. Flow sensor 122 is contained within handpiece 112.

In use, tip 150 is connected to fluid source 126 through sensor 122 through irrigation lines 130, 132 and 134. Sensor 122 measures the flow of irrigation fluid from source 126 to tip 150 and supplies this information to CPU 116 through cable 136. CPU 116, through cable 138, may open and close valve 124 so as to vary the amount of irrigation fluid reaching tip 150 from source 126. CPU 116 may also, through cable 140, vary the output of power supply 120 being sent to handpiece 112 through power cable 142. CPU 116 may also use data supplied by sensor 122 to vary the operation of pump 118 through cable 144, which aspirates fluid from handpiece 112 through line 146 and into collection container 128 through line 148. CPU 116 may also use data supplied by sensor 122 and the applied output of power supply 120 to provide audible tones to the user.

Figure 3:
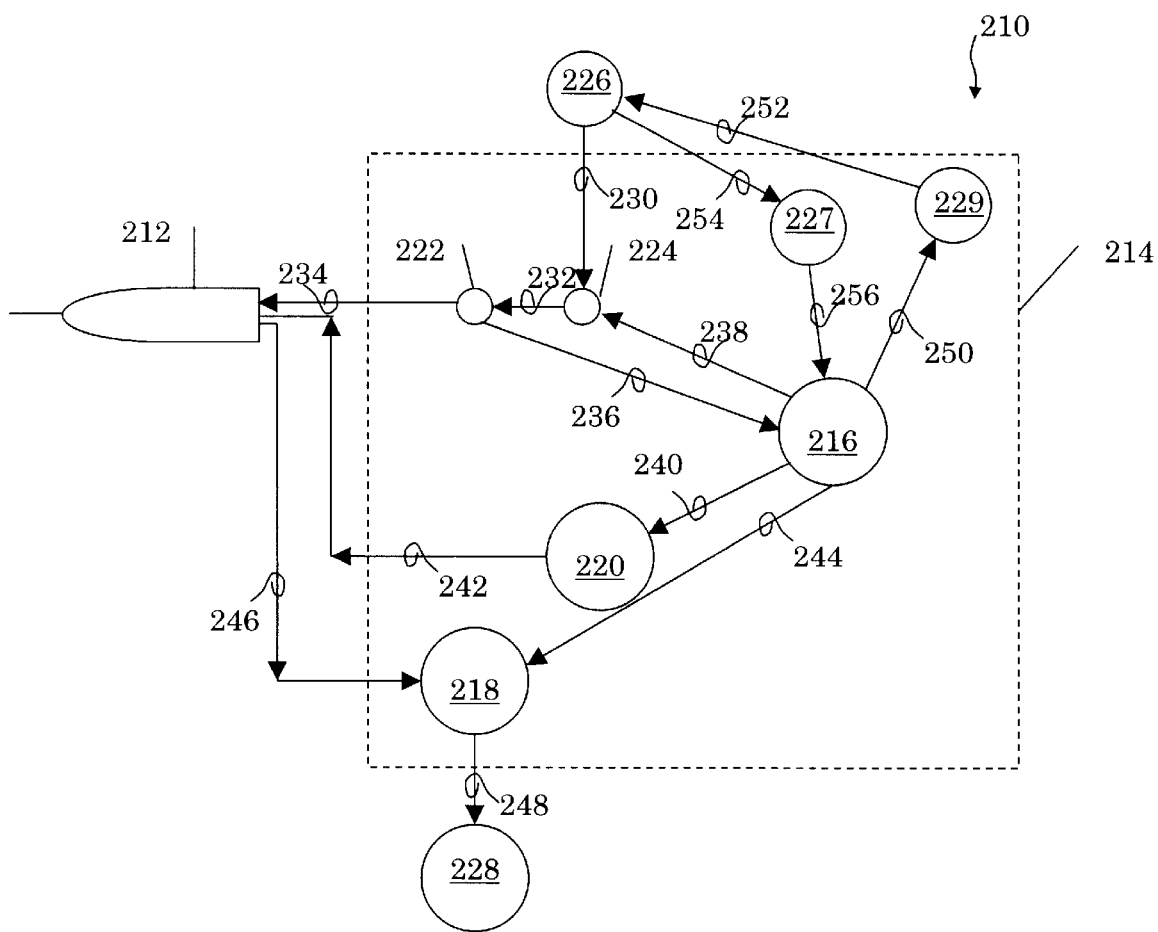
FIG. 3 is a block diagram of a third embodiment of a control system that can be used with the present invention showing the flow sensor in the instrument and pressurized infusion control of the infusion source.

As seen in FIG. 3, in a third embodiment of the present invention, control system 210 for use in operating handpiece 212 includes control console 214. Control console 214 generally includes control module or CPU 216, aspiration pump 218, handpiece power supply 220, valve 224, pressurizing source 229, and pressure sensor 227. Flow sensor 222 is connected to handpiece 212 and infusion fluid source 226 through irrigation lines 230, 232 and 234. Infusion source 226 may be any commercially available irrigation solution provided in bottles. Pressurizing source 229 pressurizes infusion source 226 through line 252 and is controlled by CPU 216 through cable 250. Pressurizing source 229 may be any commercially available pressure controller, such as incorporated in the ACCURUS® surgical system available from Alcon Laboratories, Inc., Fort Worth, Tex. Pressure sensor 227 measures the pressure of infusion source 226 through lines 254 and is monitored by CPU 216 through cable 256. Pressure sensor 227 may be any suitable commercially available pressure sensor, such as Model MPX5100 available from Motorola, Inc., Phoenix, Ariz.

In use, sensor 222 measures the flow of irrigation fluid from source 226 to handpiece 212 and supplies this information to CPU 216 through cable 236. The irrigation fluid flow data may be used by CPU 216 to control the operating parameters of console 214 using software commands that are well known in the art. For example, CPU 216, through cable 250, may control pressurizing source 229 while reading pressure sensor 227 data through cable 256 so as to vary the pressure and amount of irrigation fluid reaching handpiece 212 from source 226. CPU 216 may also, through cable 240, vary the output of power supply 220 being sent to handpiece 212 through power cable 242. CPU 216 may also use data supplied by sensor 222 to vary the operation of pump 218 through line 244, which aspirates fluid from handpiece 212 through line 246 and into collection container 228 through line 248. CPU 216 may also use data supplied by sensor 222 and the applied output of power supply 220 to provide audible tones to the user.

Figure 4:
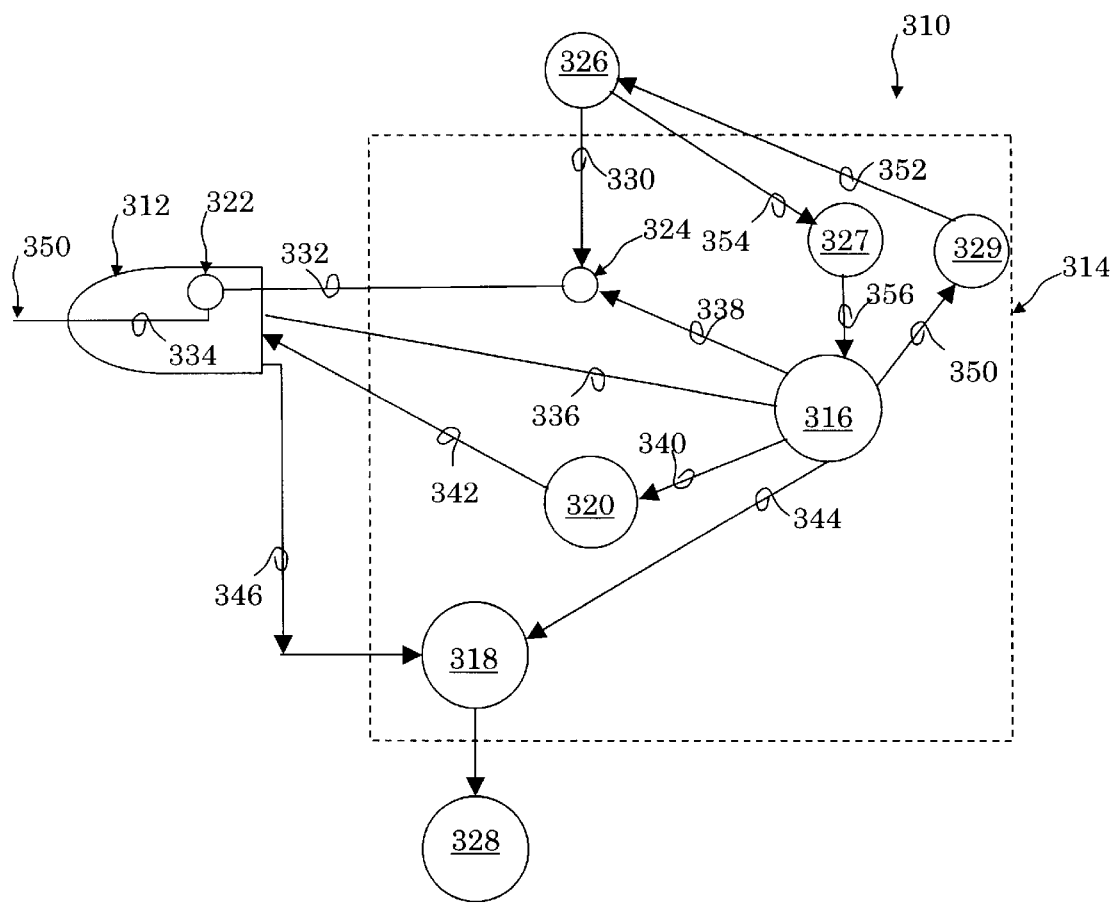
FIG. 4 is a block diagram of a fourth embodiment of a control system that can be used with the present invention showing the flow sensor in the handpiece and pressurized infusion control of the infusion source.

As seen in FIG. 4, in a fourth embodiment of the present invention, control system 310 for use in operating handpiece 312 includes control console 314. Control console 314 generally includes control module or CPU 316, aspiration pump 318, handpiece power supply 320, valve 324, pressurizing source 329, and pressure sensor 327. Flow sensor 322 is contained within handpiece 312. Infusion source 326 may be any commercially available irrigation solution provided in bottles. Pressurizing source 329 may be any commercially available pressure controller. Pressure sensor 327 may be any suitable commercially available pressure sensor.

In use, sensor 322 measures the flow of irrigation fluid from source 326 to handpiece 312 and supplies this information to CPU 316 through cable 336. The irrigation fluid flow data may be used by CPU 316 to control the operating parameters of console 314 using software commands that are well known in the art. For example, CPU 316, through cable 350, may control pressurizing source 329 while reading pressure sensor 327 data through cable 356 so as to vary the pressure and amount of irrigation fluid reaching handpiece 312 from source 326. CPU 316 may also, through cable 340, vary the output of power supply 320 being sent to handpiece 312 through power cable 342. CPU 316 may also use data supplied by sensor 322 to vary the operation of pump 318 through cable 344, which aspirates fluid from handpiece 312 through line 346 and into collection container 328 through line 348. CPU 316 may also use data supplied by sensor 322 and the applied output of power supply 320 to provide audible tones to the user.

Figure 5:
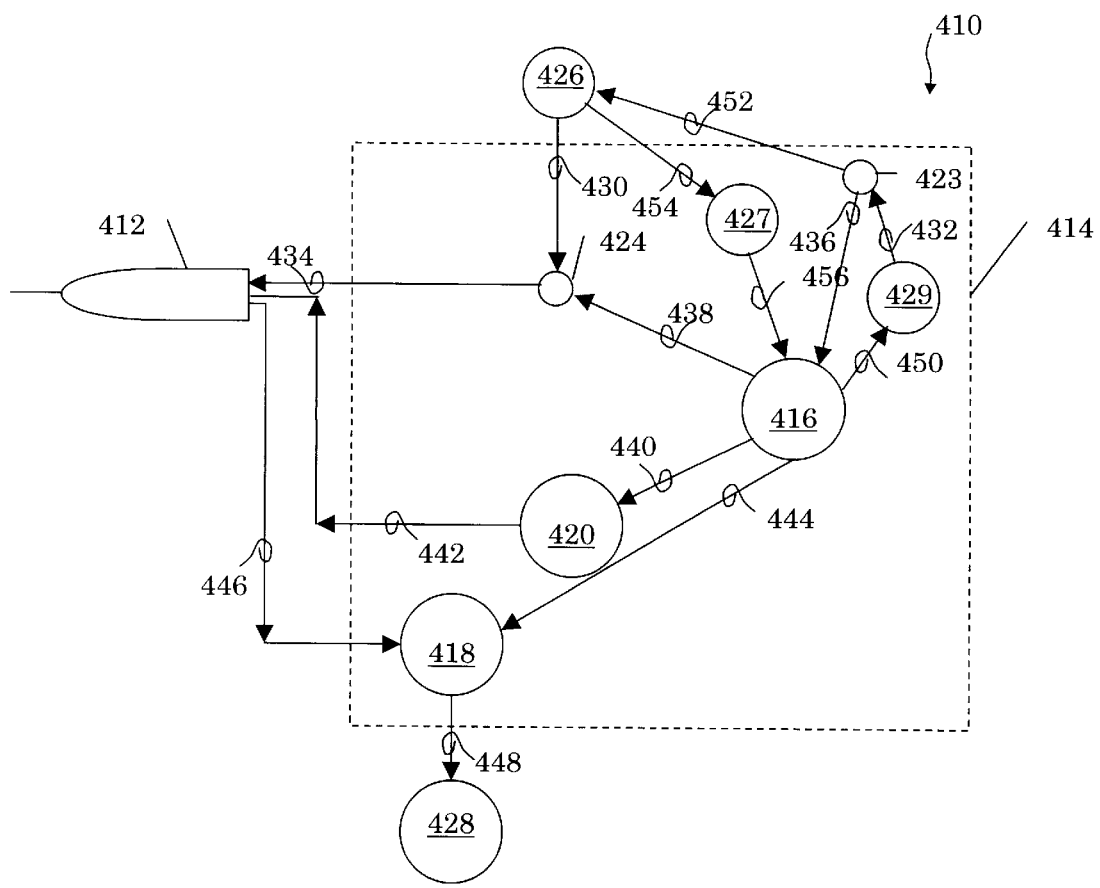
FIG. 5 is a block diagram of a fifth embodiment of a control system that can be used with the present invention showing a flow sensor in the instrument and measuring air flow of the pressurized infusion source to calculate infusion fluid flow.

As seen in FIG. 5, in a fifth embodiment of the present invention, control system 410 for use in operating handpiece 412 includes control console 414. Control console 414 generally includes control module or CPU 416, aspiration pump 418, handpiece power supply 420, valve 424, pressurizing source 429, and pressure sensor 427. Airflow sensor 423 is connected to pressurizing source 429 and infusion source 426 through lines 432 and 452. Sensor 423 may be any commercially available flow sensor, such as Model AWM3100V available from Honeywell Micro Switch, Freeport, Ill. Infusion source 426 may be any commercially available irrigation solution provided in bottles.

In use, sensor 423 measures the flow of air into the infusion source 426 and supplies this information to CPU 416 through cable 436. The airflow data may be used by CPU 416 along with information from pressure sensor 427 for the calculation of infusion flow to the handpiece through line 434. This infusion flow calculation may be used to control the operating parameters of console 414 using software commands that are well known in the art. For example, CPU 416, through cable 450, may control pressurizing source 429 while reading pressure sensor 427 data through cable 456 so as to vary the pressure and amount of irrigation fluid reaching handpiece 412 from source 426. CPU 416 may also, through cable 440, vary the output of power supply 420 being sent to handpiece 412 through power cable 442. CPU 416 may also use this infusion flow calculation to vary the operation of pump 418 through cable 444, which aspirates fluid from handpiece 412 through line 446 and into collection container 428 through line 448. CPU 416 may also use this infusion flow calculation and the applied output of power supply 420 to provide audible tones to the user.

Figure 6:
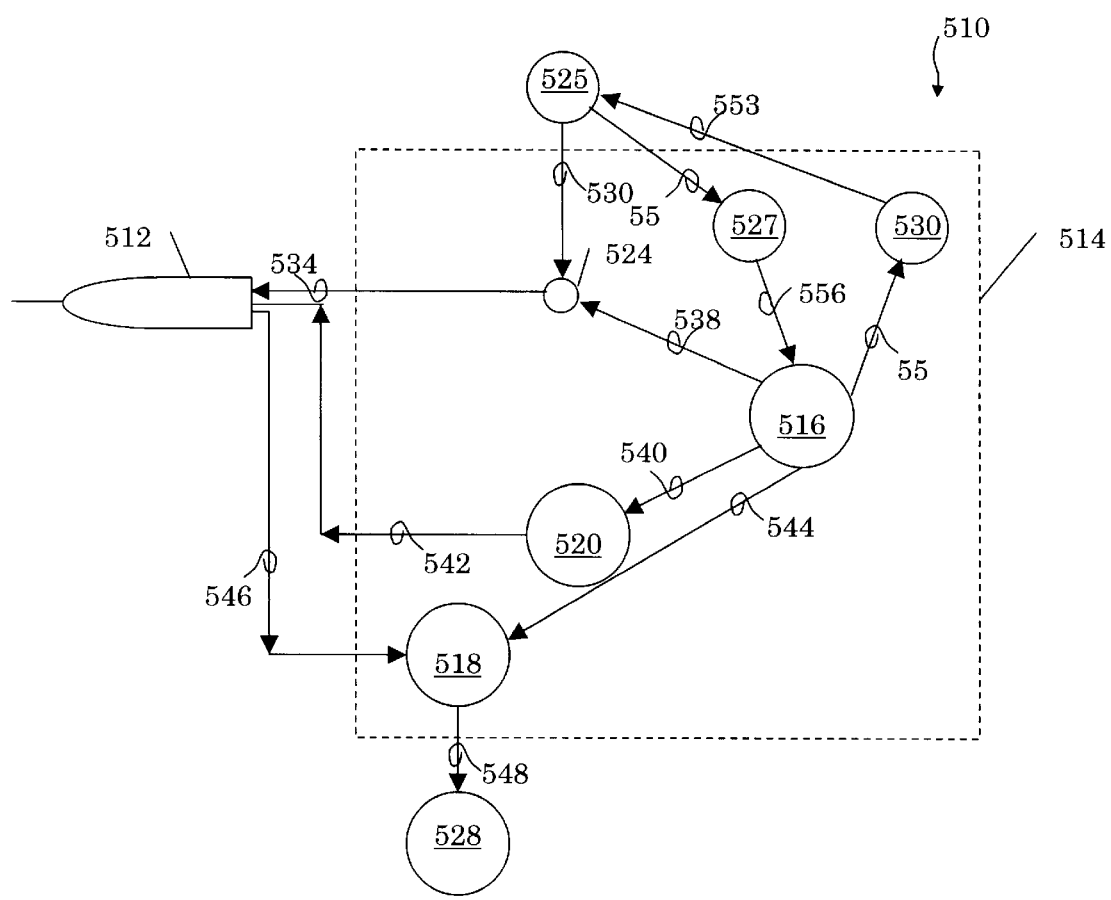
FIG. 6 is a block diagram of a sixth embodiment of a control system that can be used with the present invention showing the pressurized infusion source as a compressed compliant bag and the infusion fluid flow calculated from the rate of infusion source compression.

As seen in FIG. 6, in a sixth embodiment of the present invention, control system 510 for use in operating handpiece 512 includes control console 514. Control console 514 generally includes control module or CPU 516, aspiration pump 518, handpiece power supply 520, valve 524, pressurizing source 530, and pressure sensor 527. Infusion source 525 may be any commercially available irrigation solution provided in bags or a custom compliant container. Pressurizing source 530 is a compressing device that squeezes infusion source 525 through mechanical link 553 in order to pressurize the fluid. The rate of compression of the infusion source is controlled by CPU 516 through cable 550.

In use, CPU 516 calculates the infusion flow to the handpiece through line 534 based on the compression rate of pressurizing source 530 and the pressure data from pressure sensor 527. This infusion flow calculation may be used to control the operating parameters of console 514 using software commands that are well known in the art. For example, CPU 516, through cable 550, may control pressurizing source 530 while reading pressure sensor 527 data through cable 556 so as to vary the pressure and amount of irrigation fluid reaching handpiece 512 from source 525. CPU 516 may also, through cable 540, vary the output of power supply 520 being sent to handpiece 512 though power cable 542. CPU 516 may also use this infusion flow calculation to vary the operation of pump 518 through cable 544, which aspirates fluid from handpiece 512 through line 546 and into collection container 528 through line 548. CPU 516 may also use this infusion flow calculation and the applied output of power supply 520 to provide audible tones to the user.

Figure 7:
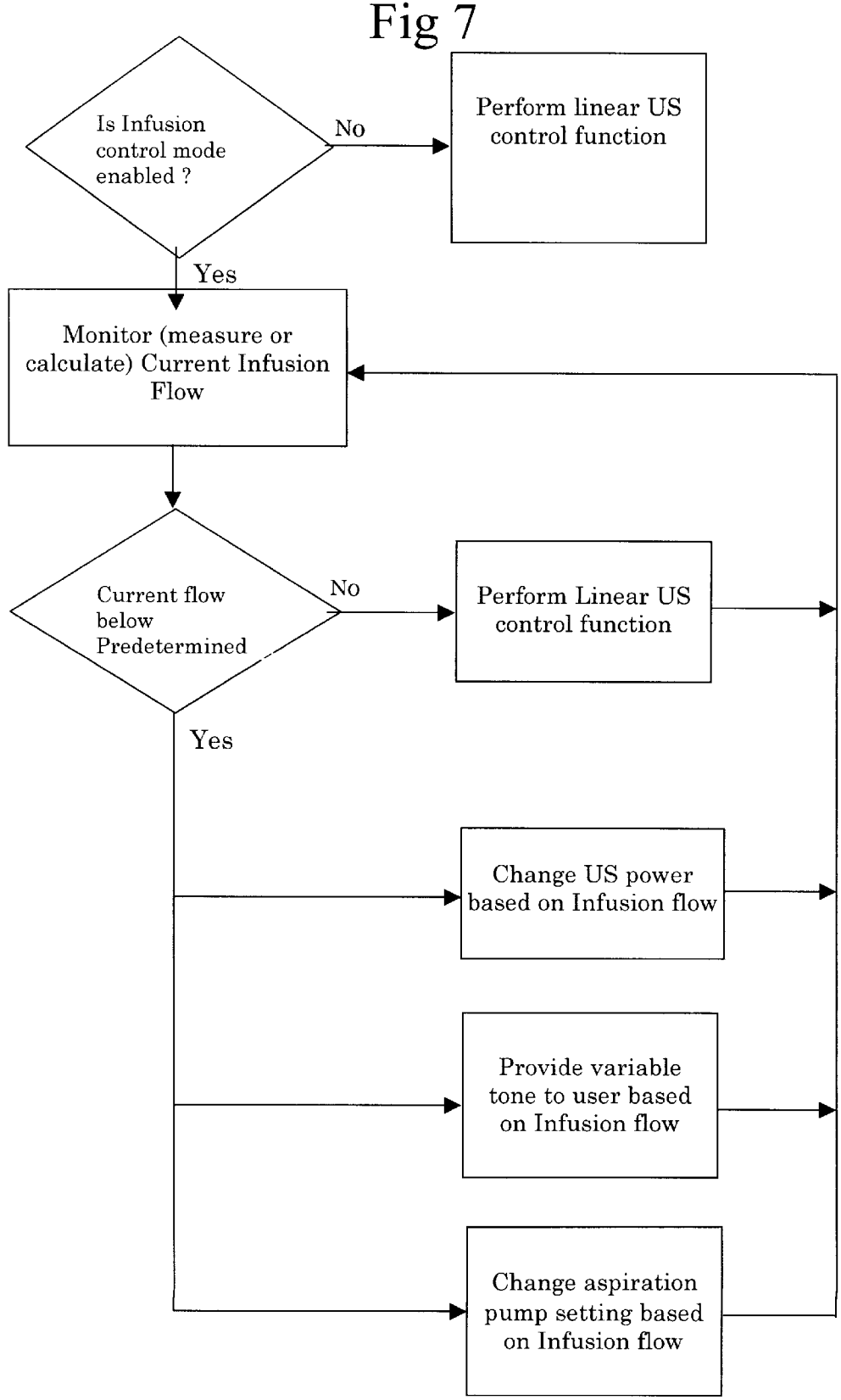
FIG. 7 is a flow chart illustrating the operation of an infusion flow control mode that can be used with the present invention.

As seen in FIG. 7, when the system of the present invention is monitoring infusion flow, the system monitors the current infusion flow and compares the actual flow against a predetermined flow rate. If infusion flow is above the predetermined rate, no action is taken by the system. If the infusion flow is below the predetermined rate, the system may take a variety of actions, such as changing the power delivered to the ultrasound handpiece, providing a variable tone to the surgeon or changing the aspiration pressure.

This description is given for purposes of illustration and explanation. It will be apparent to those skilled in the relevant art that changes and modifications may be made to the invention described above without departing from its scope or spirit.

We claim:

1. A method of controlling the operating parameters of a surgical system, the method comprising the steps of:
   a) providing a surgical system having,
      i) an aspiration pump,
      ii) a control module capable of varying the operation of the aspiration pump and
      iii) an infusion fluid flow sensor capable of providing infusion fluid flow information to the control module;
   b) setting a predetermined infusion fluid flow rate in the control module;
   c) measuring a current actual infusion fluid flow rate with the infusion fluid flow sensor and providing the current infusion fluid flow rate to the control module;
   d) comparing the current actual infusion fluid flow rate with the predetermined infusion fluid flow rate in the control module; and
   e) varying the operation of the aspiration pump if the current actual infusion fluid flow rate is below the predetermined infusion fluid flow rate.

2. A method of controlling the operating parameters of a surgical system, the method comprising the steps of:
   a) providing a surgical system having,
      i) an ultrasound handpiece,
      ii) a control module capable of varying the operation of the ultrasound handpiece and
      iii) an infusion fluid flow sensor capable of providing infusion fluid flow information to the control module;

b) setting a predetermined infusion fluid flow rate in the control module;
c) measuring a current actual infusion fluid flow rate with the infusion fluid flow sensor and providing the current infusion fluid flow rate to the control module;
d) comparing the current actual infusion fluid flow rate with the predetermined infusion fluid flow rate in the control module; and
e) varying the operation of the ultrasound handpiece if the current actual infusion fluid flow rate is below the predetermined infusion fluid flow rate.

3. A method of controlling the operating parameters of a surgical system, the method comprising the steps of:
a) providing a surgical system having,
  i) a control module capable of producing audible tones and
  ii) an infusion fluid flow sensor capable of providing infusion fluid flow information to the control module;
b) setting a predetermined infusion fluid flow rate in the control module;
c) measuring a current actual infusion fluid flow rate with the infusion fluid flow sensor and providing the current infusion fluid flow rate to the control module;
d) comparing the current actual infusion fluid flow rate with the predetermined infusion fluid flow rate in the control module; and
e) providing an audible tone if the current actual infusion fluid flow rate is below the predetermined infusion fluid flow rate.

4. A method of controlling the operating parameters of a surgical system, the method comprising the steps of:
a) providing a surgical system having,
  i) an infusion fluid source,
  ii) a source for pressurizing the infusion fluid source,
  iii) a control module capable of varying the operation of the source for pressurizing the infusion fluid source and
  iv) an infusion fluid flow sensor capable of providing infusion fluid flow information to the control module;
b) setting a predetermined infusion fluid flow rate in the control module;
c) measuring a current actual infusion fluid rate with the infusion fluid flow sensor and providing the current infusion fluid flow rate to the control module;
d) comparing the current actual infusion fluid flow rate with the predetermined infusion fluid flow rate in the control module; and
e) varying the operation of the source for pressurizing the infusion fluid source if the current actual infusion fluid flow rate is below the predetermined infusion fluid flow rate.

* * * * *